United States Patent
Kreischer et al.

(12)

(10) Patent No.: US 6,380,451 B1
(45) Date of Patent: Apr. 30, 2002

(54) METHODS FOR RESTORING THE HEAT TRANSFER COEFFICIENT OF AN OLIGOMERIZATION REACTOR

(75) Inventors: Bruce E. Kreischer; Warren M. Ewert; Ronald D. Knudsen, all of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/474,306

(22) Filed: Dec. 29, 1999

(51) Int. Cl.$^7$ .............................. C07C 2/08; B08B 9/00
(52) U.S. Cl. .................. 585/502; 585/504; 585/950; 134/22.14; 134/22.19
(58) Field of Search ................... 585/950, 502, 585/504; 134/22.14, 22.19

(56) References Cited

U.S. PATENT DOCUMENTS

| | | | | |
|---|---|---|---|---|
| 3,423,323 A | * | 1/1969 | Hunter et al. ............. | 134/22.14 |
| 3,468,849 A | * | 9/1969 | Rothert ..................... | 528/484 |
| 3,477,451 A | * | 11/1969 | Majewski ................ | 134/22.19 |
| 3,507,849 A | * | 4/1970 | Daues, Jr. ................... | 526/62 |
| 4,020,121 A | * | 4/1977 | Kister et al. ................ | 585/504 |
| 4,166,171 A | * | 8/1979 | Mitchell .................... | 528/488 |
| 4,197,398 A | | 4/1980 | Floyd et al. ................. | 528/488 |
| 4,452,975 A | * | 6/1984 | Watson et al. .............. | 528/493 |
| 4,591,391 A | * | 5/1986 | Shimizu et al. .......... | 134/22.17 |
| 4,863,524 A | * | 9/1989 | Komabashuri et al. .. | 134/22.19 |
| 4,904,309 A | * | 2/1990 | Komabashiri et al. ........ | 134/42 |
| 5,198,563 A | | 3/1993 | Reagen et al. ................ | 556/57 |
| 5,689,028 A | | 11/1997 | Lashier et al. .............. | 585/512 |
| 5,750,816 A | | 5/1998 | Araki et al. ................ | 585/512 |
| 5,750,817 A | | 5/1998 | Tanaka et al. .............. | 585/520 |
| 5,782,989 A | * | 7/1998 | Rueter ..................... | 134/22.19 |
| 5,859,303 A | | 1/1999 | Lashier ........................ | 585/513 |

* cited by examiner

*Primary Examiner*—Walter D. Griffin
(74) *Attorney, Agent, or Firm*—Hsiang-ning Sun

(57) ABSTRACT

The specification discloses a method for cleaning an oligomerization reactor after making a higher olefin in the reactor. An olefin is reacted in the presence of a catalyst comprising an aluminum alkyl to form an olefin reaction product. For example, ethylene can be trimerized in the reaction to produce 1-hexene. The reaction also causes a co-product residue of the catalyst to form on the interior surface of the reactor. The interior surface of the reactor is then contacted with an alcohol under conditions effective to remove at least a substantial amount of the catalyst residue from the interior surface of the reactor. The catalyst-removing step can be carried out by combining an alcohol with the process medium used in the reactor. The combined medium can be used to remove both the accumulated polymer co-product and the accumulated catalyst residue from the reactor.

40 Claims, No Drawings

METHODS FOR RESTORING THE HEAT TRANSFER COEFFICIENT OF AN OLIGOMERIZATION REACTOR

BACKGROUND OF THE INVENTION

This invention generally relates to olefin preparation. This invention relates more specifically to a method of cleaning co-product polymer and catalyst residues from an oligomerization reactor, such as a trimerization reactor.

Olefins, particularly alpha-olefins, also referred to herein as 1-olefins, have many uses. In addition to their uses as specific chemicals, alpha-olefins are used in polymerization processes, either as monomers or co-monomers, to prepare polyolefins. Unfortunately, during the production of higher alpha-olefins, residue can be deposited on reactor walls and other surfaces of the reactor. This residue can build up on the interior walls, other portions of the reactor, inhibit heat transfer, and cause the reactor to overheat.

The problem of polymer co-product build-up and its effect on the heat transfer efficiency of a reactor is discussed in U.S. Pat. No. 5,689,028, the entirety of which is herein incorporated by reference.

A "hot wash" method has been devised, employing the process medium used at a higher temperature than the normal reaction temperature, to remove polymer residue from the reactor wall. The hot wash method has considerably alleviated the problem of heat transfer efficiency in olefin reactors, but the heat transfer efficiency of the reactor surfaces still goes down, or decreases, as the reactor is used over a period of time.

An alcohol, referred to here as a "catalyst kill agent," previously has been added to the catalyst charge in the effluent of an olefin oligomerization reactor. See, for example, U.S. Pat. No. 5,689,028 discloses adding 2-ethylhexanol to the reactor effluent of a trimerization reactor to deactivate the catalyst system; U.S. Pat. No. 5,859,303, Example 1, discloses that addition of an alcohol deactivates the catalyst system; U.S. Pat. No. 5,750,816 teaches the addition of alcohols, phenols, carboxylic acids, primary or secondary amines, or ammonia, for example 1-hexanol (Example 13), to the effluent of the ethylene trimerization reactor. The '816 patent teaches generally that this step "maintain[s] the dispersed state of principally the catalyst components in the reaction dispersion, . . . in the process line from the outlet of the oligomerization reactor to the inlet of the distillation tower"; U.S. Pat. No. 5,750,816, col. 12, lines 20–23 and 49–67; U.S. Pat. No. 5,750,817 discloses the use of ethanol to terminate an ethylene trimerization reaction.

SUMMARY OF THE INVENTION

The inventors have discovered that catalyst residue, as well as polymer residue, can build up on the walls of an oligomerization reactor. This problem particularly has been noticed in connection with the use of catalyst systems including or made from aluminum alkyls. Catalyst residue can have a substantial effect on the heat transfer efficiency of the reactor walls. While the catalyst residue can build up more slowly than polymer residue, over time this catalyst residue can substantially reduce the heat transfer efficiency of the reactor, even if the problem of polymer build-up has been adequately addressed. None of the patents identified above disclose or suggest that catalyst residue can build up in an oligomerization reactor. None of these patents is believed to teach how to prevent or eliminate such a build-up.

Accordingly, one object of the invention is to provide a method for removing residue from the wall of an olefin reactor.

Another object of the invention is to improve the heat transfer efficiency of a reactor that has developed a residue or build up of catalyst systems.

An additional object of the invention is to remove a substantial proportion, if not all, of the residues from the walls of an olefin reactor.

One or more of the preceding objects, or one or more other objects which will become plain upon consideration of the present specification, are satisfied in whole or in part by the invention described here.

One aspect of the invention is a method for cleaning a reactor in which a higher olefin has been made, using a catalyst system. The reactor has an interior surface on which a catalyst residue has been deposited. The method is carried out by contacting the interior surface of the reactor with an alcohol. The contacting step is accomplished under conditions effective to remove at least a substantial amount of the catalyst residue from the interior surface of the reactor.

Another aspect of the invention is a method for making a higher olefin. An olefin is reacted in a reactor, in the presence of a catalyst system. The reaction forms a higher olefin reaction product, but also can generate a co-product residue of the catalyst system to deposit on the interior surface of the reactor. The interior surface of the reactor then is contacted with an alcohol. This alcohol-contacting step is carried out under conditions effective to remove at least a substantial amount of the catalyst residue from the interior surface of the reactor.

One significant advantage of the invention is that the heat transfer efficiency of the reactor wall ordinarily would diminish with time and use, even if the polymer build-up were addressed. When the present invention is carried out, the catalyst residue deposit on the reactor wall is at least partially removed, resulting in an increase in the heat transfer efficiency of the reactor wall. In some instances, the heat transfer efficiency of the cleaned reactor wall can be as great as, or even slightly greater than, that of an unused reactor wall. This is a significant, previously unappreciated advantage of practicing the present invention.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims. The mention of or statement of a preference for certain embodiments does not indicate an intent to exclude other embodiments that are not mentioned or stated to be preferred.

The reaction contemplated here broadly relates to oligomerization of ethylene and other lower olefins to produce higher olefins. In this context, "lower" and "higher" are relative; a lower alpha-olefin is converted to a higher olefin, or higher alpha-olefin, having a greater number of carbon atoms. The reaction is carried out in the presence of one or more catalyst systems under conditions encouraging the reaction to proceed.

The present invention will be exemplified in the context of a trimerization reaction, although it is contemplated that the invention can find use in other oligomerization reactions.

"Trimerization," as used in this disclosure, is defined as any combination of any two, three, or more olefins reducing the number of olefin, i.e., carbon-carbon double bonds by two. For example, the three olefin bonds in the combination of three ethylene units can be reduced by two, to one olefin bond, in 1-hexene. In another example, the four olefin bonds in the combination of two 1,3-butadiene units, can be reduced by two, to two olefin bonds in 1,5-cyclooctadiene.

As used here, the term "trimerization" is intended to include dimerization of diolefins, as well as "co-trimerization," each as further discussed below. The reactants, catalysts, equipment, and reaction conditions useful in the present process and the reaction products and co-products formed as a result of the trimerization reaction are further described below. Additionally, while the term "trimerization", as defied above, is used throughout this disclosure, this invention also encompasses oligomerization reactions and processes.

Reactants

The reactants applicable for use in the trimerization process of this invention include olefinic compounds which can self-react, i.e., trimerize, to give useful products. For example, the self-reaction of ethylene can give 1-hexene, and the self-reaction of 1,3-butadiene can give 1,5-cyclooctadiene.

The reactants applicable for use in the trimerization process of this invention also include olefinic compounds which can react with other olefinic compounds, i.e., co-trimerize, to give useful products. For example, co-trimerization of ethylene plus 1-hexene can give decenes, including 1-decene. Co-trimerization of ethylene and 1-butene can give octenes, including 1-octene. Co-trimerization of 1-decene and ethylene can give tetradecenes, including 1-tetradecene.

Suitable trimerizable olefin compounds are those compounds having from about 2 to about 30 carbon atoms per molecule and having at least one olefinic double bond. Exemplary olefins include, but are not limited to, acyclic olefins and diolefins.

Acyclic olefins are contemplated such as, for example, ethylene, propylene, 1-butene, 2-butene, 1-pentene, 2-pentene, 1-hexene, 2-hexene, 3-hexene, 1-heptene, 2-heptene, 3-heptene, the four normal octenes, the four normal nonenes, and mixtures of any two or more of those.

Exemplary diolefin compounds contemplated here include, but are not limited to, 1,3-butadiene, 1,4-pentadiene, and 1,5-hexadiene.

If branched or cyclic olefins are used as reactants, while not wishing to be bound by theory, it is believed that steric hindrance could hinder the trimerization process. Therefore, the branched or cyclic portion of the olefin generally will be distant from the. carbon-carbon double bond. The present invention is not limited to use with the olefins suggested by this theory to be useful. In accordance with the present invention, any olefin that can be active in a trimerization or oligomerization reaction can be used.

Catalyst Systems

One trimerization catalyst system contemplated in accordance with this invention is a three-part system comprising the combination of a chromium source, a pyrrole-containing compound and one or more metal alkyls. Catalyst system of this invention further can comprise a halide or halide source. Optionally, the catalyst system can be supported on an inorganic oxide support. These catalyst systems are especially useful for the dimerization and trimerization of olefins, such as, for example, ethylene to 1-hexene. For the present purposes, any catalyst or catalyst system including a metal alkyl is more broadly contemplated.

The chromium source can be one or more organic or inorganic compounds, in which the chromium oxidation state is from 0 to 6. Generally, the chromium source will have a formula of $CrX_n$, in which each X can be the same or different, and can be any organic or inorganic radical, and n is an integer from 1 to 6. Exemplary organic radicals can have from about 1 to about 20 carbon atoms per radical, and can be alkyl alkoxy, ester, ketone, carboxy, or amido radicals, for example. The organic radicals can be straight-chained or branched, cyclic or acyclic, aromatic or aliphatic, can be made of mixed aliphatic, aromatic, or cycloaliphatic groups. Exemplary inorganic radicals include, but are not limited to, any anion or oxidizing radical, for example, halides, sulfates, or oxides.

Preferably, the chromium source is a chromium (II)- or chromium (III)-containing compound that can yield a catalyst system with improved oligomerization or trimerization activity.

Most preferably, the chromium source is a chromium (III) compound because of its ease of use, availability, and enhanced catalyst system activity. Exemplary chromium (III) compounds include, but are not limited to, chromium carboxylates, chromium naphthenates, chromium halides, chromium pyrrolides, and chromium dionates. Specific exemplary chromium (III) compounds (followed in some instances below by their respective abbreviations) include, but are not limited to, chromium (III) 2,2,6,6,-tetramethylheptanedionate ($Cr(TMHD)_3$); chromium (III) 2-ethylhexanoate ($Cr(EH)_3$); chromium (III) tris-(2-ethylhexanoate); chromium (III) naphthenate ($Cr(Np)_3$); chromium (III) chloride; chromic bromide; chromic fluoride; chromium (III) acetylacetonate; chromium (III) acetate; chromium (III) butyrate; chromium (III) neopentanoate; chromium (III) laurate; chromium (III) stearate; chromium (III) pyrrolides; chromium (III) oxalate; or combinations of two or more of those.

Specific exemplary chromium (II) compounds include, but are not limited to, chromous bromide; chromous fluoride; chromous chloride; chromium (II) bis-(2-ethylhexanoate); chromium (II) acetate; chromium (II) butyrate; chromium (II) neopentanoate; chromium (II) laurate; chromium (II) stearate; chromium (II) oxalate; chromium (II) pyrrolides; or combinations of two or more of those. Chromium (II) and chromium (III) compounds also can be combined.

The pyrrole-containing compound of the catalyst system can be any one, two or more of those that can react with a chromium source to form a chromium pyrrolide complex. As used in this disclosure, the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide" is defined as a compound comprising a 5-membered nitrogen-containing heterocycle, such as for example, pyrrole, derivatives of pyrrole, and mixtures of two or more of those.

Broadly, the pyrrole-containing compound can be pyrrole or any heteroleptic or homoleptic metal complex or salt containing a pyrrolide radical or ligand. The pyrrole-containing compound can be either affirmatively added to the reaction or generated in-situ.

Generally, the pyrrole-containing compound has from about 4 to about 20 carbon atoms per molecule. Exemplary pyrrolides, mentioned because of their high reactivity and activity with the other reactants, include hydrogen pyrrolide (pyrrole); lithium pyrrolide; sodium pyrrolide; potassium pyrrolide; cesium pyrrolide; the salts of substituted pyrrolides; or combinations of two or more of those. The useful substituted pyrrolides include, but are not limited to pyrrole-2-carboxylic acid; 2-acetylpyrrole; pyrrole-2-carboxaldehyde; tetrahydroindole; 2,5-dimethylpyrrole; 2,4-dimethyl-3-ethylpyrrole; 3-acetyl-2,4-dimethylpyrrole; ethyl-2,4-dimethyl-5-(ethoxycarbonyl)-3-pyrrole-proprionate; ethyl-3,5-dimethyl-2-pyrrolecarboxylate; or combinations of two or more of those. When the pyrrole-containing compound contains chromium, the resultant chromium compound can be called a chromium pyrrolide.

The most preferred pyrrole-containing compounds useful in trimerization catalyst systems can be selected from the group consisting of hydrogen pyrrolide, i.e., pyrrole ($C_4H_5N$), 2,5-dimethylpyrrole or chromium pyrrolides because of enhanced trimerization activity. Optionally, for ease of use, a chromium pyrrolide can provide both the chromium source and the pyrrole-containing compound. As used in this disclosure, when a chromium pyrrolide is used to form a catalyst system, a chromium pyrrolide is considered to provide both the chromium source and the pyrrole-containing compound. While all pyrrole-containing compounds can produce catalyst systems with high activity and productivity, use of pyrrole or 2,5-dimethylpyrrole can produce a catalyst system with enhanced activity and selectivity to a desired product.

The metal alkyl of the catalyst system can be any heteroleptic or homoleptic metal alkyl compound. One or more metal alkyls can be used. The alkyl ligands on the metal can be aliphatic, aromatic, or both (if more than one ligand is present). Preferably, the alkyl ligands are any saturated or unsaturated aliphatic radical.

The metal alkyl can have any number of carbon atoms. However, due to commercial availability and ease of use, the metal alkyl usually comprises less than about 70 carbon atoms per metal alkyl molecule and preferably less than about 20 carbon atoms per molecule.

Exemplary metal alkyls include, but are not limited to, alkylaluminum compounds, alkylboron compounds, alkylmagnesium compounds, alkylzinc compounds or alkyl lithium compounds. Exemplary metal alkyls include, but are not limited to n-butyl lithium; sec-butyllithium; tert-butyllithium; diethylmagnesium; diethylzinc; triethylaluminum; trimethylaluminum; triisobutylaluminum; or combinations of two or more of those.

Preferably, the metal alkyl is selected from the group consisting of non-hydrolyzed (i.e., not pre-contacted with water) alkylaluminum compounds, derivatives of alkylaluminum compounds, halogenated alkylaluminum compounds, and mixtures of two or more of those. Mixed metal alkyls can provide improved product selectivity, as well as improved catalyst system reactivity, activity, or productivity. The use of hydrolyzed metal alkyls can result in decreased olefin, i.e. liquids, production and increased polymer, i.e. solids, production.

Most preferably, the metal alkyl is a non-hydrolyzed alkylaluminum compound expressed by the general formulas $AlR_3$, $AlR_2X$, $AlRX_2$, $AlR_2OR$, $AlRXOR$, or $Al_2R_3X_3$, in which Al is an aluminum atom, each R is an alkyl group, O is an oxygen atom, and X is a halogen atom. Exemplary compounds include, but are not limited to triethylaluminum; tripropylaluminum; tributylaluminum; diethylaluminum chloride; diethylaluminum bromide; diethylaluminum ethoxide; diethylaluminum phenoxide; ethylaluminum dichloride; ethylaluminum sesquichloride; and mixtures of two or more of those for best catalyst system activity and product selectivity. One preferred single alkylaluminum compound is triethylaluminum, for the best catalyst system activity and product selectivity. Most preferably, the alkyl aluminum compound is a combination of triethyl aluminum (TEA) and diethyl aluminum chloride (DEAC).

While not wishing to be bound by theory, it is believed that a halide containing-compound can improve product purity and selectivity. Bromide-containing compounds can improve catalyst system activity, but chloride-containing compounds are more economical and, thus, more preferred. Any chloride-containing compound can be used, such as, for example, DEAC and organo chlorides. Exemplary organo chlorides include, but are not limited to, carbon tetrachloride, methylene chloride, chloroform, benzylchloride, hexachloroethane and mixtures thereof.

One particular composite catalyst contemplated here is the combination of chromium (III) ethylhexanoate, 2,5-dimethylpyrrole, triethylaluminum, and diethylaluminum chloride. This composite catalyst can be used to trimerize ethylene, forming 1-hexene. U.S. Pat. No. 5,198,563, the entirety of which is herein incorporated by reference, teaches the use of a suitable trimerization catalyst for the present invention.

Media

Usually, the chromium source, the pyrrole-containing compound, and the metal alkyl are combined in an olefinically or aromatically unsaturated hydrocarbon reaction medium. The hydrocarbon can be any aromatic or aliphatic hydrocarbon, in a gaseous, liquid or solid state. Preferably, to thoroughly contact the chromium source, pyrrole-containing compound, and metal alkyl, the hydrocarbon is used in a liquid state.

The hydrocarbon can have any number of carbon atoms per molecule. Usually, the hydrocarbon will comprise less than about 70 carbon atoms per molecule, and preferably, less than about 20 carbon atoms per molecule, due to the commercial availability and ease of use of low-molecular-weight compounds. The most preferred hydrocarbon compound is a reaction product formed by use of the catalyst system. For example, if 1-hexene is a reaction product, some of the 1-hexene product can be recycled for use as a reaction medium.

Exemplary unsaturated aliphatic hydrocarbon compounds contemplated for use as catalyst reaction media include, but are not limited to, ethylene, 1-hexene, 1,3-butadiene, and mixtures of two or more of those. Exemplary unsaturated aromatic hydrocarbons useful as reaction media include, but are not limited to, benzene, toluene, ethylbenzene, xylene, mesitylene, hexamethylbenzene, and mixtures of two or more of those. Unsaturated aromatic hydrocarbons are preferred to improve the stability of the catalyst system and to produce a highly active and selective catalyst system. The most preferred unsaturated aromatic hydrocarbon is ethylbenzene.

The trimerization process is generally carried out in a solution or slurry of the catalyst components, including the reaction medium, in an inert medium or diluent. Broadly, common diluents are fluid paraffins, cycloparaffins, or aromatic hydrocarbons. Exemplary reactor diluents include, but are not limited to, isobutane, cyclohexane, and methylcyclohexane. Isobutane can be used for enhanced compatibility with known olefin polymerization processes. However, a homogenous trimerization catalyst system is more easily dispersed in cyclohexane. Therefore, a preferred diluent for a homogeneous catalyst system trimerization process is cyclohexane.

The catalyst system comprising a chromium source, pyrrole-containing compound, metal alkyl, and reaction media can contain additional components that do not adversely affect and can enhance the resultant catalyst system, such as, for example, halides.

Equipment

The trimerization reaction is conveniently carried out in a suitable reactor, commonly a continuous-feed autoclave reactor with a fluid jacket or internal heat transfer coil and a suitable stirring mechanism (commonly either mechanical stirring or an inert gas, typically nitrogen, purge), piping and valves. For example, a loop reavctor with mechanical stirring, such as, for example, a stirring pump can be used.

The reactor has an interior surface on which an undesirable catalyst residue or polymer co-product is deposited as the reactor is used to catalytically trimerize olefins. The "interior surface" as used herein, can be the reactor wall; the outer surface of the heat transfer coil; valves and piping in, adjacent to, or downstream of the reactor proper; thermocouples other instrumentation, probes, or equipment in contact with the charge in the reactor; or any other surface that is exposed to the contents of the reactor.

Some problems associated with deposition of solid co-products and residue on the interior surfaces are a reduction in the efficiency of heat transfer through the surface, a reduction in the effective capacity or cross-section of a vessel or piping, interference with the operation of mechanical elements such as valves or mechanical stirring mechanisms, and other problems that are known to those skilled in the art.

Reaction Conditions

Reaction products, as defined in this specification, can be prepared from the catalyst systems of this invention by dispersion reaction, slurry reaction, or gas phase reaction techniques using conventional equipment and contacting processes. Contacting of the monomer or monomers with a catalyst system can be effected by any manner known in the art. One convenient method is to suspend or dissolve the catalyst system in an organic medium and to agitate the mixture to maintain the catalyst system in dispersion or solution throughout the trimerization process. Other known contacting methods can also be employed.

For example, the trimerization process can be carried out in a slurry of the catalyst components in an inert medium or diluent which is the process medium. Broadly, the common diluents are fluid paraffins, cycloparaffins, or aromatic hydrocarbons. Exemplary reactor diluents include, but are not limited to, isobutane, cyclohexane, and methylcyclohexane. Isobutane can be used for enhanced compatibility with known olefin polymerization processes. However, a homogenous trimerization catalyst system is more easily dispersed in cyclohexane. Therefore, a preferred diluent for a homogeneous catalyzed trimerization process is cyclohexane.

In accordance with another embodiment of this invention, a slurry process can be carried out in a diluent (medium), which is a product of the olefin oligomerization process. Therefor, the choice of reactor diluent, or medium, is based on the selection of the initial olefin reactant. For example, if the oligomerization catalyst is used to trimerize ethylene to 1-hexene, the solvent for the oligomerization reaction would be 1-hexene. If ethylene and hexene were trimerized to produce 1-decene, the oligomerization reaction solvent would be 1-decene. If 1,3-butadiene was trimerized to 1,5-cyclooctadiene, the trimerization reactor solvent would be 1,5-cyclooctadiene.

Commonly, the catalyst system and reaction media are introduced to the reactor either continuously or in one or more charges, and the olefin reactant is continuously or intermittently introduced throughout the reaction as a gas under pressure. The pressure in the reactor commonly is maintained by adding the olefin at a suitable rate to replace the olefin consumed by the reaction.

Hydrogen gas also can be charged to the reactor during the reaction to improve the rate of reaction and enhance the catalytic activity and desired trimer product selectivity. The presence of hydrogen also can be helpful for reducing co-product polymers into a powdery, non-tacky form that is easily removed from the reactor and easily separated from the effluent, as by filtering. Optionally, the powdery, non-tacky co-product polymer can be separated and eluted with the heavies. The partial pressure of hydrogen present is usually from about 0.1 to about 100 kg/cm$^2$ (about 1 to 1000 N/cm$^2$), preferably from about 0.1 to about 80 kg/cm$^2$ (about 1 to 800 N/cm$^2$).

The reaction temperature employed can be any temperature that can trimerize the olefin reactants. Generally, reaction temperatures are within a range of from about 0° C. to about 250° C. Preferably, reaction temperatures within a range of from about 60° C. to about 200° C. and most preferably, within a range of from about 80° C. to about 150° C. are employed. When the reactant is predominately ethylene, a temperature in the range of from about 0° C. to about 300° C. generally can be used. Preferably, when the reactant is predominately ethylene, a temperature in the range of from about 60° C. to about 150° C. is employed. If the reaction temperature is too low, the polymer tends to stick to the reactor surfaces. If the reaction temperature is too high, the catalyst system and reaction products may decompose.

The overall reaction pressure employed can be any pressure that can trimerize the olefin reactants. Generally, reaction pressures are within a range of from about atmospheric pressure 0 psig (0 N/cm$^2$ gauge pressure) to about 2500 psig (about 1700 N/cm$^2$ gauge pressure). Preferably, reaction pressures within a range of from about atmospheric pressure to about 1000 psig (690 N/cm$^2$ gauge pressure), and most preferably within a range of 300 to 900 psig (about 200 to about 620 N/cm$^2$ gauge pressure), are employed. If the reaction pressure is too low, the catalyst system activity may be too low. The maximum pressure generally is dictated by safety concerns and the desire for vessels having walls no thicker than necessary.

The charge in the reactor can be agitated or stirred by an inert gas (e.g. nitrogen) purge, by introducing the reactant, hydrogen, fluid medium, or catalyst system or exhausting the effluent in a manner causing agitation, by mechanical or magnetic stirring, or in any other suitable manner.

The reaction can be run continuously by steadily charging reactant, catalyst system, and process medium and removing the liquid contents of the reactor. For example, a continuous stirred tank reactor system can be employed that includes feed systems for the catalyst, reagent and medium and a discharge system for the effluent. A batch process can also be employed, however.

Usually the catalyst kill agent is added to prior to any separations to kill the remainder of the catalyst. Then, the reactor effluent can be treated to separate products, and recycle any residual reactants, medium, catalyst components, and other components suitable for recycling.

The trimerization reaction is exothermic, so the reaction temperature is commonly regulated by circulating cooling water through a jacket or heat transfer coil, thus transferring heat out of the reactor. It is important to be able to transfer heat efficiently out of the reactor, so the reactor can be effectively maintained at the desired temperature and the heat can be removed using a minimum quantity of the cooling medium. Another advantage of more effective heat transfer is that the reaction can be run at a higher throughput for a given temperature, which improves production efficiency.

After the catalyst system has been used to prepare one or more olefin products, the reactor effluent stream comprising olefin trimer products, catalyst system, and some polymer or higher oligomer co-products, can be contacted with an alcohol to "kill" or deactivate the catalyst system.

Any alcohol that can be easily dispersed in the reactor effluent stream can be used. For example, lower alcohols such as methanol, ethanol, propanol, isopropanol, etc. can kill the catalyst system. Preferably, however, an alcohol is selected that has a boiling point, or molecular weight, such that the alcohol will not form an azeotrope with the olefin monomer product.

In an exemplary process, in which the catalyst system is used to trimerize ethylene to 1-hexene, a monofunctional alcohol with six or more carbon atoms per molecule is preferred. Most preferably, a monofunctional alcohol having six to twelve carbon atoms per molecule is used for best catalyst system deactivation. Such alcohols can be easily removed from the 1-hexene olefin product. Exemplary monofunctional alcohols include, but, are not limited to, 1-hexanol; 2-hexanol; 3-hexanol; 2-ethyl-1-hexanol, 3-octanol, 1-heptanol; 2-heptanol; 3-heptanol; 4-heptanol; 2-methyl-3-heptanol; 1-octanol; 2-octanol; 3-octanol; 4-octanol; 7-methyl-2-decanol; 1-decanol; 2-decanol; 3-decanol; 4-decanol, 5-decanol, 2-ethyl-1-decanol; and mixtures of two or more of those.

Alternatively, a low-molecular-weight diol or polyol can be used as a catalyst kill agent, for example ethylene glycol. Diols and polyols commonly have much higher boiling points than monoalcohols of comparable molecular weight, and so can be separated more easily from 1-hexene.

Enough alcohol is added to the reactor effluent stream to deactivate, or "kill", the olefin production catalyst system and to inhibit, or halt, the production of undesirable solids, particularly polymer or catalyst solids. If an insufficient amount of alcohol is used, any metals in the catalyst system, such as chromium or aluminum, can precipitate and can interfere with future effluent processing. Generally, the amount of alcohol added can be up to about 5 molar equivalents of alcohol per total moles of metals in the effluent stream. Preferably, the amount of alcohol added is from about 1 to about 4 molar equivalents, and most preferably the amount of alcohol added is from about 1.8 to about 2.5 molar equivalents of alcohol per mole of metals in the reactor effluent stream.

After the catalyst system has been deactivated, or "killed," olefin products, such as, for example, 1-hexene, can be removed. Any removal process can be used, although distillation is preferred for ease of use. First, decenes, spent catalyst system and polymer co-product can be removed from all other components, Then, in a simple distillation, ethylene is removed from the reaction product, and then 1-hexene and reactor medium are distilled away from the reaction dispersion while the catalyst system components are concentrated and recovered together with the co-product polymer. The concentrated dispersion containing co-product polymer and catalyst system components can be discarded, or can be further treated as described below.

The product stream produced by the ethylene trimerization process usually comprises butene; 1-hexene; internal hexenes (i.e. 2-hexene or 3-hexene); octenes; decenes, and "heavies", wherein "heavies" includes spent catalyst system, co-product polymer and olefins having greater than about ten carbon atoms per molecule.

Removing Residues

The trimerization process commonly produces two residues that can build up on the internal surfaces of the reactor.

One residue, long recognized to build up on the walls of the reactor, is an oligomer or a polymer having a chain length higher than the intended product, formed as a co-product. This higher oligomer or polymer residue is referred to here as "polymer residue." For example, in the case of an ethylene reaction, polyethylene or paraffin wax residue can be formed and build up on the internal surfaces of the reactor. This polymer residue can detract from the heat transfer efficiency of the internal surfaces of the reactor.

Polymer residue can be removed from a trimerization reactor by washing the reactor with a solvent for the residue. The trimerization reactor commonly is supplied with a solvent for co-product polymers, such as, for example, cyclohexane or methylcyclohexane, as the process medium. When a polymer solvent is used as the process medium, the same process medium can be used to periodically flush out the reactor. The washing conditions can be more stringent than the usual process conditions, in order to remove the polymer residue that is not removed under the usual process conditions. For example, the washing step can be a "hot wash," carried out by circulating the usual process medium at a higher temperature than the process temperature to melt, more quickly dissolve, or otherwise dislodge polymer residue.

In a continuous ethylene trimerization process, the hot wash can be carried out as follows. The reaction can be halted by stopping the feed of catalyst system and reactants while continuing to inject and drain the reactor medium, i.e. cyclohexane or methylcyclohexane, and increasing the medium temperature by 60° C. to 70° C. The hot wash can be continued for several hours, or as long as necessary to remove all or substantially all polymer residue. This hot wash has been found to remove the buildup of polymer residue.

A second residue, which the present inventors have found also can detract substantially from the heat transfer efficiency of the reactor, is referred to here as catalyst residue. The inventors have not determined the exact chemical composition of this catalyst residue. It can be a precipitate or deposit of the entire catalyst system or one or more of the catalyst system components, the product of a reaction between the catalyst system components, the catalyst system and the reactor wall, spent catalyst system constituents, a combination of these residues, or something else. The residue is believed to be associated with the catalyst system, though the present invention is not limited by the accuracy of that theory.

According to the present invention, one material useful for breaking down and allowing the removal of this catalyst residue is an alcohol. Suitable alcohols for this purpose include the catalyst kill agent alcohols, as described above. As with the catalyst kill agent alcohols, it is useful here to employ an alcohol that is easily separable from (for example, does not form an azeotrope with) the trimerization product and other reaction constituents.

The alcohol can be introduced to contact the catalyst residue on the interior surfaces of the reactor in a variety of ways.

As one example, the alcohol can be added to the process medium during the hot wash, thus removing the polymer and catalyst residues together. A convenient proportion of the alcohol in the process medium is from about 0.01 ppm (mg/kg) to about 10% by weight, preferably from about 0.01 ppm to about 1% by weight, and most preferably from about 1 ppm to about 3000 ppm.

After the hot wash is carried out as described previously in a continuous reactor, the reactor can be returned to service by: (1) stopping the feed of alcohol, (2) continuing the feed of the process medium until the effluent temperature returns to the working process temperature (thus flushing the alcohol out of the reactor), (3) resuming the feed of the catalyst until its concentration is adequate to resume the reaction, then (4) resuming the reactant feed and thus restarting the reaction.

As another example, an alcohol can be added to the charge in the reactor at the end of a batch process, or just before a continuous process is shut down, to prevent or remove the buildup of catalyst residue on the interior surfaces of the reactor. As used in this disclosure, "prevention" or "removal" of catalyst residue are both referred to as "removal," for ease of use. Thus, "removal" means either preventing catalyst residue from forming or removing already-formed catalyst residue. In this example, the temperature of the reactor can be increased to improve the removal of both the polymer and the catalyst residues at the same time.

The alcohol added to the reactor to clean out catalyst residue can also partially or completely kill the catalyst in the remaining charge of reactor contents. Thus, the alcohol feed into the effluent to kill the catalyst during continuous operation can be moderated or discontinued during the reactor cleaning process sequence.

However the process is carried out, the catalyst killing process is very exothermic, so heat commonly must be removed as the catalyst residue is removed. Since the reactor commonly is set up to remove heat, this requirement is easily met by circulating a cooling fluid as usual during the catalyst residue removing reaction.

In one contemplated embodiment, a continuous trimerization process can be shut down every few weeks and the reactor hot washed, which in this embodiment may require 6–9 hours. More frequent or less frequent hot wash treatments may also be employed, within the scope of the invention.

In another embodiment, a more frequent, much shorter hot wash can be introduced into the production cycle to reduce or eliminate the need for the conventional, long-duration hot wash carried out every few weeks. Longer periods of operation between shutdowns can thus be scheduled, which may prove more efficient.

It may also prove useful to hot wash the reactor conventionally and hot wash it with a medium containing alcohol on different schedules. For example, if the catalyst residue builds up more slowly than the polymer residue, the reactor can be hot washed more frequently than it is washed with an alcohol additive.

In any case disclosed above, the alcohol can be removed from the reactor effluent by distillation, just as the catalyst kill agent is conventionally removed from the reactor effluent. Optionally, the washing effluent can be passed through the same distillation apparatus used for isolating the trimerized reaction product. Using this effluent treatment, minimal changes to the process are required to allow removal of residues from the interior surfaces of the reactor.

A further understanding of how to make and use the present invention and its advantages will be provided by reference to the following example.

EXAMPLE

It has been found that if polymer and catalyst residues are removed according to the present process, the heat transfer efficiency of the reactor can be restored at least substantially to that of the reactor when new. For example, in a particular installation, it was found that production of 1-hexene alternated with the conventional hot wash cycle resulted in a heat transfer coefficient of from about 50 to about 150 BTU/hr/ft$^2$/°F. (0.028–0.085 W/cm$^2$/°C.). Subsequent use of the inventive hot wash cycle improved the heat transfer coefficient to about 167–193 BTU/hr/ft$^2$/°F. (about 0.0947–0.109 W/cm$^2$/°C.) in the same reactor. The same reactor, when brand new, had a heat transfer coefficient of about 164–171 BTU/hr/ft$^2$/°F. (0.093–0.097/cm$^2$/°C.). The present invention thus provides a significant increase in the efficiency of heat transfer of a reactor. The data are presented in Table 1 below.

TABLE 1

| Run Number | Wash Step | Heat Transfer Values (BTU/hr/ft$^2$/° F.) |
|---|---|---|
| 101 | Clean reactor, 1–2 weeks in service | 163.5 |
| 102 | Clean reactor, 1–2 weeks in service | 170.8 |
| 103 | Normal solvent hot wash | 115.0 |
| 104 | Normal solvent hot wash | 122.6 |
| 105 | Normal solvent hot wash | 115.3 |
| 106 | Normal solvent hot wash | 136.1 |
| 107 | Normal solvent hot wash | 131.7 |
| 108 | Normal solvent hot wash | 151.3 |
| 109 | 2-Ethylhexanol added to hot wash | 183.9 |
| 110 | 2-Ethylhexanol added to hot wash | 192.9 |
| 111 | 2-Ethylhexanol added to hot wash | 166.6 |
| 112 | 2-Ethylhexanol added to hot wash | 170.8 |

While this invention has been described in detail for the purpose of illustration, it is not to be construed as limited thereby but is intended to cover all changes and modifications within the spirit and scope thereof.

That which is claimed is:

1. A method for cleaning a reactor in which a higher olefin has been made using a catalyst system comprising metal content, thereby forming a catalyst residue, wherein said method comprises:

a) providing a reactor having an interior surface on which catalyst residue has been deposited;

b) contacting said interior surface with an alcohol under conditions to provide a removal of said catalyst residue from said interior surface.

2. A method according to claim 1, wherein said higher olefin is 1-hexene.

3. A method according to claim 1, wherein said alcohol has at least six carbon atoms per molecule.

4. A method according to claim 1, wherein said alcohol is separable from said higher olefin by distillation.

5. A method according to claim 1, wherein said alcohol is 2-ethylhexanol.

6. A method according to claim 1, wherein said interior surface has a build-up of a polymer residue, further comprising the step of contacting said polymer residue with a solvent for said polymer residue.

7. A method according to claim 6, wherein said solvent is selected from cyclohexane and a substituted cyclohexane.

8. A method according to claim 6, wherein said solvent is methylcyclohexane.

9. A method according to claim 6, wherein said solvent is a process medium for making said higher olefin.

10. A method according to claim 6, wherein a composition comprising said solvent and said alcohol is introduced into said reactor to provide a removal of said catalyst residue and said polymer residue from said interior surface in a single step.

11. A method according to claim 1, wherein said interior surface is a heat transfer surface and said contacting step is carried out under conditions effective to improve the heat transfer rate through said surface.

12. A method according to claim 1, wherein said contacting step is carried out by adding said alcohol to a reactor containing a reacted charge of said higher olefin and said catalyst, thereby killing said catalyst system while removing deposited catalyst residue from said reactor surface.

13. A method according to claim 12, wherein said alcohol is added in a molar ratio of up to about 5, in relation to the total metal content of said catalyst system.

14. A method for making a higher olefin, comprising:
a) providing a reactor having an interior surface;
b) in said reactor, reacting an olefin in the presence of a catalyst system comprising an aluminum alkyl, thereby forming an olefin reaction product and forming a catalyst residue on said interior surface, and
c) contacting said interior surface with an alcohol under conditions to provide a removal of said catalyst residue from said interior surface.

15. A method according to claim 14, wherein said olefin reaction product is removed before said contacting step.

16. A method according to claim 15, wherein said contacting step is carried out by washing said interior surface with a composition comprising from about 0.01 ppm (mg/kg) to about 10% by weight of said alcohol.

17. A method according to claim 14, wherein said reacting step is continuous.

18. A method according to claim 14, wherein said reacting step is carried out by continuously feeding at least one reactant, a catalyst system, and a process medium to said reactor and continuously withdrawing an effluent from said reactor, while maintaining a reaction temperature.

19. A method according to claim 18, wherein said contacting step and said reacting step are carried out alternately.

20. A method according to claim 19, wherein said contacting step is carried out by:
a) interrupting the feeds of said reactant and said catalyst,
b) continuing the feed of said process medium,
c) feeding an alcohol to said reactor, and
d) increasing the temperature of said process medium above said reaction temperature.

21. A method for cleaning a reactor in which a higher olefin has been made using a catalyst system comprising metal content, thereby forming a catalyst residue, wherein said method comprises:
a) providing a reactor having an interior surface on which catalyst residue has been deposited;
b) contacting said interior surface with a composition consisting essentially of one or more alcohols under conditions to provide a removal of said catalyst residue from said interior surface.

22. A method according to claim 21, wherein said higher olefin is 1-hexene.

23. A method according to claim 21, wherein said one or more alcohols have at least six carbon atoms per molecule.

24. A method according to claim 21, wherein said one or more alcohols are separable from said higher olefin by distillation.

25. A method according to claim 21, wherein said one or more alcohols is 2-ethylhexanol.

26. A method according to claim 21, wherein said interior surface has a build-up of a polymer residue, further comprising the step of contacting said polymer residue with a solvent for said polymer residue.

27. A method according to claim 26, wherein said solvent is selected from cyclohexane and a substituted cyclohexane.

28. A method according to claim 26, wherein said solvent is methylcyclohexane.

29. A method according to claim 26, wherein said solvent is a process medium for making said higher olefin.

30. A method according to claim 26, wherein a composition consisting essentially of said solvent and said one or more alcohols is introduced into said reactor to provide a removal of said catalyst residue and said polymer residue from said interior surface in a single step.

31. A method according to claim 21, wherein said interior surface is a heat transfer surface and said contacting step is carried out under conditions effective to improve the heat transfer rate through said surface.

32. A method according to claim 21, wherein said contacting step is carried out by adding said composition to a reactor containing a reacted charge of said higher olefin and said catalyst, thereby killing said catalyst system while removing deposited catalyst residue from said reactor surface.

33. A method according to claim 32, wherein said composition is added in a molar ratio of up to about 5, in relation to the total metal content of said catalyst system.

34. A method for making a higher olefin, comprising:
a) providing a reactor having an interior surface;
b) in said reactor, reacting an olefin in the presence of a catalyst system comprising an aluminum alkyl, thereby forming an olefin reaction product and forming a catalyst residue on said interior surface, and
c) contacting said interior surface with a composition consisting essentially of one or more alcohols under conditions to provide a removal of said catalyst residue from said interior surface.

35. A method according to claim 34, wherein said olefin reaction product is removed before said contacting step.

36. A method according to claim 35, wherein said contacting step is carried out by washing said interior surface with a process medium comprising said composition in a range of from about 0.01 ppm (mg/kg) to about 10% by weight.

37. A method according to claim 34, wherein said reacting step is continuous.

38. A method according to claim 34, wherein said reacting step is carried out by continuously feeding at least one reactant, a catalyst system, and a process medium to said reactor and continuously withdrawing an effluent from said reactor, while maintaining a reaction temperature.

39. A method according to claim 38, wherein said contacting step and said reacting step are carried out alternately.

40. A method according to claim 39, wherein said contacting step is carried out by:
 a) interrupting the feeds of said reactant and said catalyst,
 b) continuing the feed of said process medium,
 c) feeding said composition to said reactor, and
 d) increasing the temperature of said process medium above said reaction temperature.

* * * * *